United States Patent [19]

Roberts

[11] Patent Number: 5,412,996
[45] Date of Patent: May 9, 1995

[54] TESTING EQUIPMENT AND METHOD OF MANUFACTURING THE SAME

[75] Inventor: Joseph E. Roberts, Savannah, Ga.

[73] Assignee: Roberts Testing Equipment, Inc., Savannah, Ga.

[21] Appl. No.: 10,251

[22] Filed: Jan. 28, 1993

[51] Int. Cl.⁶ ............................................. G01N 3/08
[52] U.S. Cl. ................................................... 73/830
[58] Field of Search ................ 73/826, 828, 830, 834, 73/837; 228/135, 139, 178, 256, 257; 52/259, 344, 393, 730.2, 724

[56] References Cited

U.S. PATENT DOCUMENTS

| | | | |
|---|---|---|---|
| 2,754,065 | 7/1956 | Hawley | 228/139 |
| 3,010,311 | 11/1961 | Meldrum et al. | 73/828 |
| 3,849,871 | 11/1974 | Kaunitz | 228/256 |
| 4,040,220 | 8/1977 | Henager | 52/259 |
| 4,874,152 | 10/1989 | Roberts . | |
| 5,265,476 | 11/1993 | Khachaturian et al. | 73/828 |

*Primary Examiner*—Robert Raevis
*Attorney, Agent, or Firm*—Diller, Ramik & Wight

[57] ABSTRACT

A testing machine includes a pair of spaced side-by-side rails spanned by a carriage and opposite thereto a piston/cylinder mechanism between each rail and an associated crosshead. A wire cable, sling or the like is connected between the carriage and the crosshead and when the pistons of the piston/cylinder mechanisms are forcefully extended from the cylinders the sling is brought under tension loading upwardly to 3,000,000 lbs. Each side rail is formed of a plurality of sections with each section being defined by relatively long metal rail members joined by tubes and carrying studs and a first series of rebars. A second series of rebars spans a joint between adjacent rail sections. The metal rail members of adjacent sections are spaced from each other to define a gap therebetween. Concrete is poured into the sections to eventually surround, embed and unitize the sections upon subsequent solidification of the concrete. After the concrete has cured, a molten zinc alloy is poured into the gaps or spaces between adjacent metal elongated members and eventually solidifying therein.

22 Claims, 3 Drawing Sheets

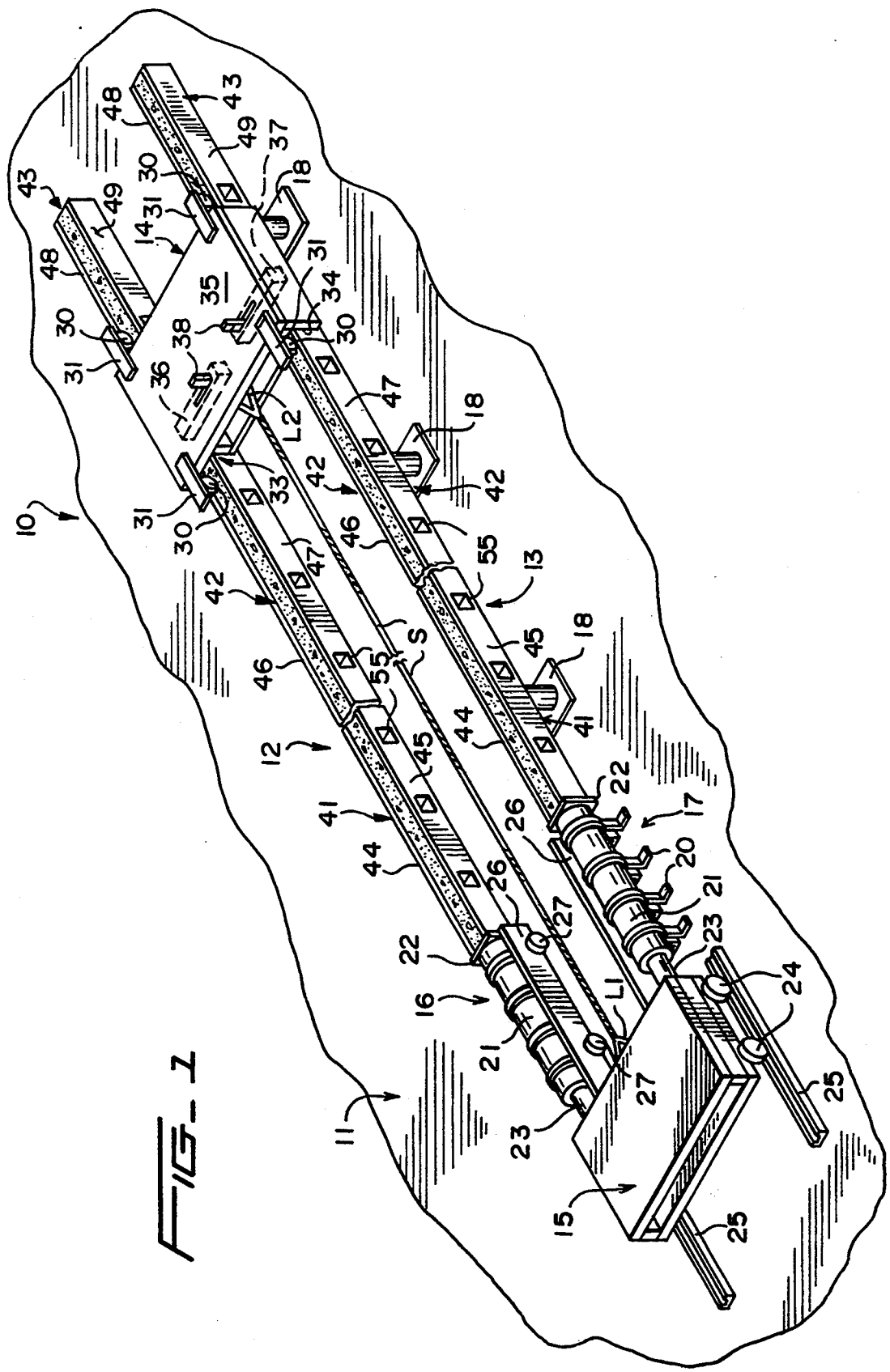

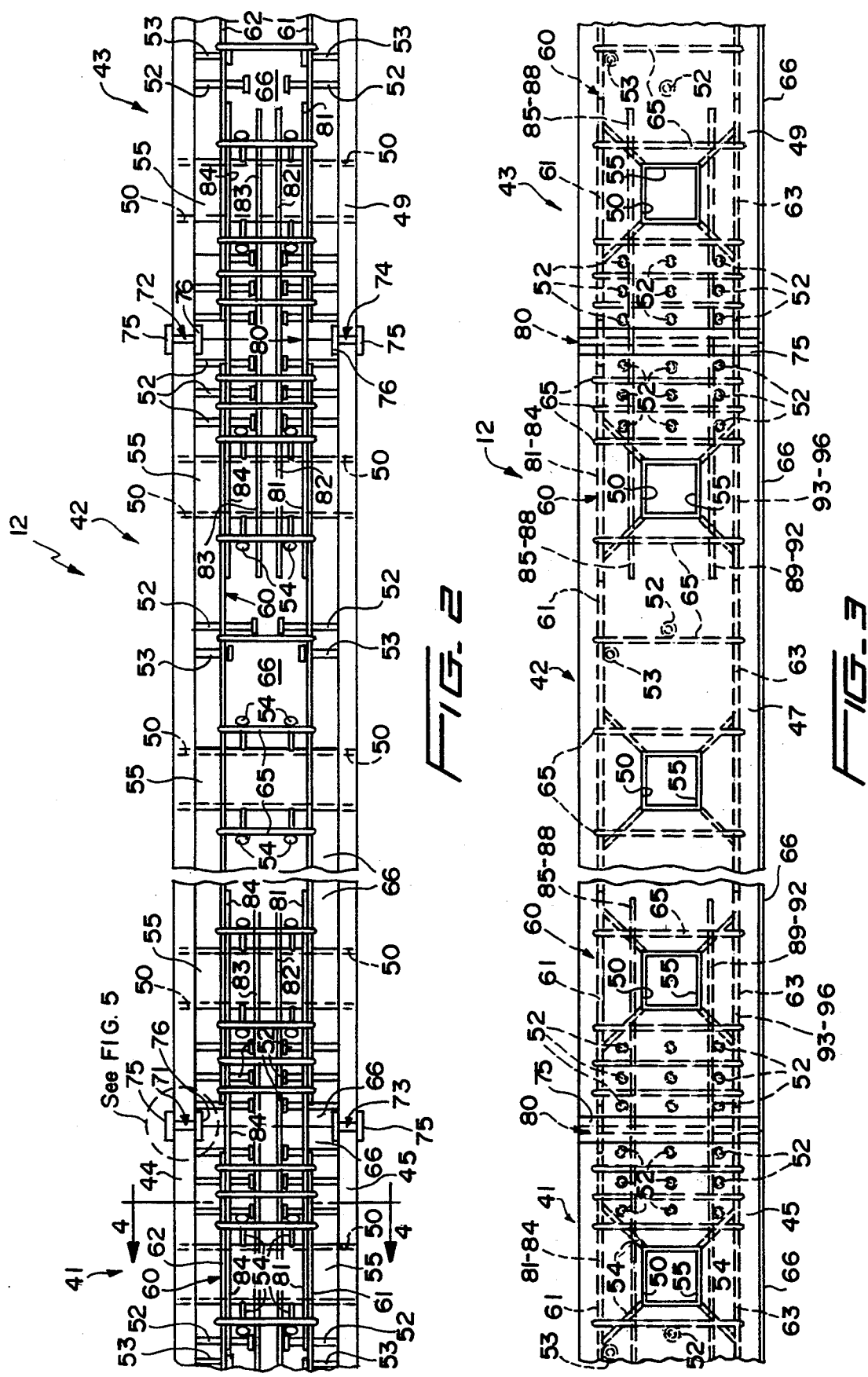

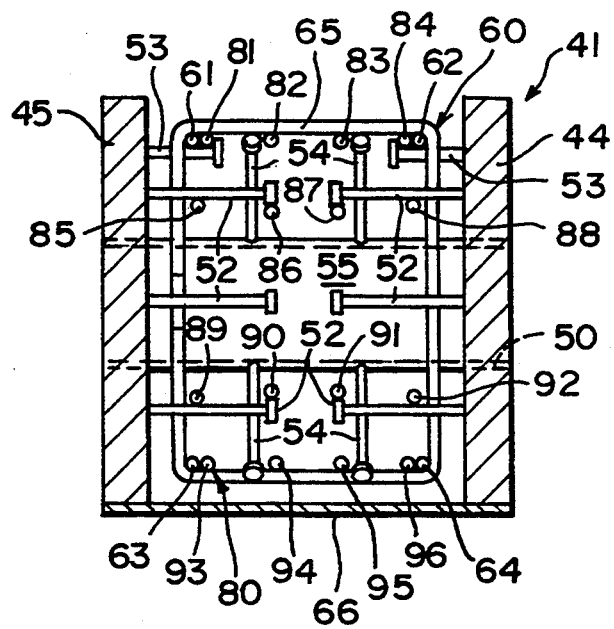
FIG._4
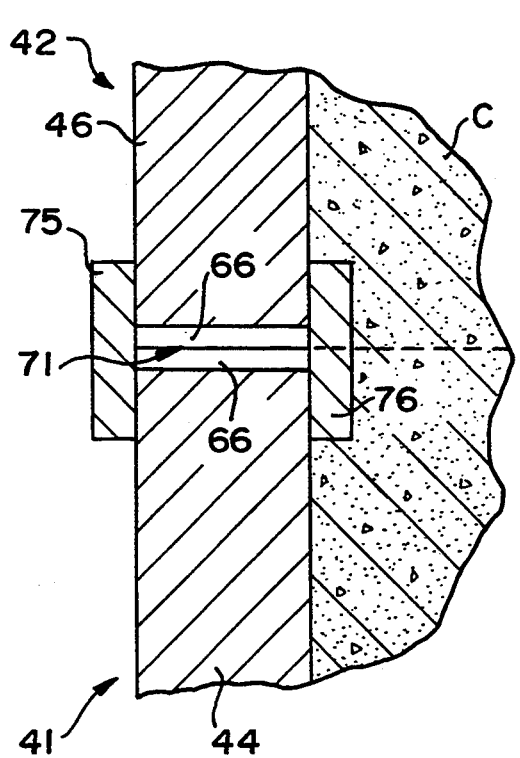
FIG._5
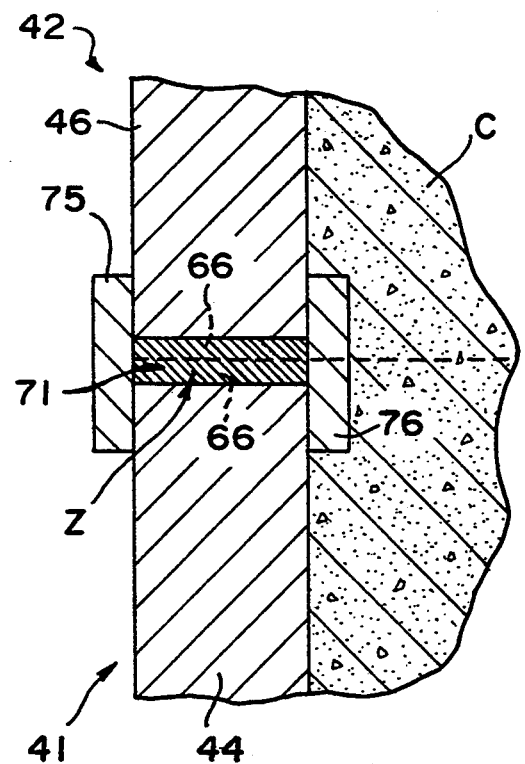
FIG._6

TESTING EQUIPMENT AND METHOD OF MANUFACTURING THE SAME

BACKGROUND OF THE INVENTION

This invention is directed to testing equipment which can subject wire ropes, cables, slings and the like to extremely high loads, namely, up to 3,000,000 lbs. In conventional testing equipment of the type to which this invention is directed, a pair of parallel laterally spaced rails are supported upon a test bed and are spanned by a carriage or yoke assembly to which is secured one end of a sling which is to be tested. Each rail is formed from a plurality of heavy/thick cross-sectioned metal beams or members which are welded end-to-end to each other. A pair of hydraulic cylinders are arranged one between each rail and another carriage or crosshead to which the other end of the sling is connected. When the hydraulic cylinders are progressively pressurized, the sling is progressively loaded in tension and appropriate strain gauges, digital readout meters, etc. are used during standardized testing up to a certain capacity or up to sling breakage.

When the sling is loaded in tension during testing the rails are loaded in compression, and when the sling breaks the compression load of the rails is instantaneously transformed into a tension load from the rebound or recoil effect. Therefore, such conventional rails, which can be 200' long, must be able to carry both compression and tension loads and resist deterioration/fracture/bending when under load and when there is an instantaneous reversal in loading from rail compression to rail tension upon the fracture of a sling or the like.

In the past rails of 200' or longer that can carry compression or tension loads were made by making a 100% weld at the butt joints between the individual thick cross-sectioned metal beams or members. The problem with rails manufactured by butt-welding metal rail members to each other are at least twofold, namely, keeping the overall rail straight during and after welding because of the tremendous heat which will cause the metal rail members to warp and the high cost involved in the materials and the welding process. It is absolutely critical that the rails are straight, and if the individual rail members are warped or misaligned because of the welds, either coaxially relative to each other or relative to the rail arranged parallel thereto, the test load cannot be properly distributed, applied to the sling and/or absorbed under breakage and recoil.

SUMMARY OF THE INVENTION

In keeping with the foregoing, a primary object of the present invention is a novel testing machine or similar testing equipment which is specifically designed such that the rails thereof are extremely strong in both compression and tension in the absence of utilizing full penetration or similar welds at the joints of relatively thick cross-sectioned individual rail members, as has been conventional practice. The method of manufacturing the rails of the present invention is cost effective and efficient, and the rails manufactured thereby are stable, free of warpage and can be loaded to design maximums under tension and compression loading and abrupt reversals therebetween.

The testing equipment includes a pair of parallel rails, a crosshead, a carriage and a pair of hydraulic cylinders with the latter being disposed one between each rail and the crosshead, as is conventional. However, in lieu of heavy or thick cross-sectioned rail members welded to each by, for example, a 100% full penetration weld at the joints of the rail members, each rail is instead manufactured by the following general procedure.

(a) A plurality of metal studs are welded normal to and selectively along what will eventually become the inner surface of each of a pair of relatively long/elongated heavy cross-sectioned metal rail members which are placed in side-by-side parallel relationship to each other and are joined by polygonal tubes laterally spanning and welded to the pair of rail members to form a rail member frame. The space or distance between the rail members is approximately $1\frac{1}{2}'$ and the length is upwards to 45', although the dimensions can vary depending upon the overall testing loads which are to be generated by the test equipment. Each rail member is also approximately $1\frac{1}{2}'$ high and is 2" thick.

(b) A plurality of elongated metal reinforcing bars or rebars run the length of each rail member frame and optionally can project beyond the ends thereof. As an example, if the rebars are 55' long, approximately 5' of rebar would project from each of the axially opposite ends of each rail member frame. The rebars are wired to the studs and/or to polygonal metal stirrups which are in turn positioned along the length of each rail member frame. A thin ($\frac{1}{8}$") steel plate is welded in spanning relationship between and along the entire length of each rail member frame to essentially form a closed bottom or wall and transform each rail member frame into a reinforced rail member box section.

(c) A plurality of such factory manufactured reinforced rail member sections are forwarded to the site at which the test equipment is to be installed and used, and on-site a first plurality of the rail member sections are aligned with each other end-to-end with opposing ends of the metal rail members being slightly spaced from each other to form spaces or gaps therebetween.

(d) A second plurality of the rail member sections are similarly aligned with each other end-to-end again with opposing ends of the metal rail members slightly spaced from each other to form spaces or gaps therebetween. The gaps or spaces of the first and second plurality of rail member sections are laterally aligned, and the first and second rail member sections are spaced laterally from each other approximately 10' and, of course, in parallel relationship to each other.

(e) Each of the gaps between adjacent metal rail members is spanned by plates welded to inner and outer surfaces thereof, and a plate is also welded in spanning relationship to close the bottom of each gap and span the bottom plates of adjacent rail member sections.

(f) Additional metal reinforcing elements or rebars are then positioned to span the distance between and project well into each of the rail member sections. As an example, these additional reinforcing rebars might be 10' in length and thus span the gaps/spaces and project 5' into each adjacent rail member section. The additional rebars are wired to the studs and/or the stirrups and/or the rebars earlier wired to the rail member frames.

(g) Concrete is then poured into the rail member sections filling the same totally from end-to-end which might be, for example, in the vicinity of 200' of concrete which eventually solidifies in situ and thus unitizes all of the aligned rail member sections to each other.

(h) Once the concrete in each rail member section has solidified, a molten zinc alloy is poured into the gaps/spaces between all opposing rail members which when solidifies will carry/transfer the compressive load when a sling is under tension testing. The concrete also carries the compressive load while additionally stiffening and rigidifying each of the joints between adjacent rail member sections and adding weight to the overall structure. Since the joints between endwise adjacent rail member sections are also loaded with special high strength rebar loaded in tension long enough to develop their tension strength during the concrete solidification, the joints are also as strong in tension as they are in compression.

With the above and other objects in view that will hereinafter appear, the nature of the invention will be more clearly understood by reference to the following detailed description, the appended claims and the several views illustrated in the accompanying drawings.

BRIEF DESCRIPTION OF THE DRAWINGS

FIG. 1 is a schematic perspective view of a novel testing machine or testing equipment constructed in accordance with this invention, and illustrates a pair of rails bridged by a carriage or yoke assembly, a hydraulic piston/cylinder associated with each rail and another carriage or crosshead, and a sling connected between the crosshead and the carriage which can be loaded in tension during testing as the piston/cylinders are pressurized.

FIG. 2 is an enlarged fragmentary top plan view of one of the rails of FIG. 1, and illustrates a plurality of rail member sections in aligned end-to-end relationship housing studs, rebar and stirrups and a gap between the opposing ends of a rail member of each adjacent rail member section.

FIG. 3 is a fragmentary side elevational view of the rail member sections of FIG. 2, and further illustrate the studs, rebar and stirrups together with polygonal tubes spanning and welded to the rail members.

FIG. 4 is an enlarged cross-sectional view taken generally along line 4—4 of FIG. 2 and illustrates two of the rail members of one of the rail member sections and a polygonal tube, the rebars, studs, stirrups and a thin metal plate enclosing the bottom of the rail member section.

FIG. 5 is an enlarged fragmentary horizontal cross-sectional view of the encircled portion of FIG. 2 and illustrates a pair of plates welded to inner and outer surfaces of adjacent rail members in spanning relationship to a gap or space therebetween and concrete inboard of the rail members.

FIG. 6 is a fragmentary cross-sectional view similar to FIG. 5 and illustrates the gap or space of FIG. 5 filled with an initially molten and subsequently solidified zinc alloy.

DESCRIPTION OF THE PREFERRED EMBODIMENT

A novel testing machine or like test equipment for testing a relatively elongated product, such as a heavy cable, wire rope, wire sling or the like, is fully illustrated in FIG. 1 of the drawings and is generally designated by the reference numeral 10.

The testing machine 10 is located at an appropriate test site and is supported upon and atop an appropriately reinforced foundation 11.

The testing machine 10 includes several major components, namely, a yoke assembly or carriage 14, a pair of relatively long side-by-side parallel side rails 12, 13 which are of identical construction and constitute the novelty of the present invention, another carriage or crosshead 15, and a pair of identical hydraulic piston/cylinder mechanisms 16, 17.

A plurality of support legs or pedestal supports 18 are positioned beneath and along the underside of the side rails 12, 13 and support the side rails 12, 13 in parallel laterally spaced relationship. Similar support legs or pedestal supports 20 are conventionally secured to cylinders 21 of each of the piston/cylinder mechanisms 16, 17 to support the piston/cylinder mechanisms 16, 17 in alignment with the respective side rails 12, 13. Each of the cylinders 21 carries an end plate 22 which is welded or otherwise rigidly attached to each respective cylinder 21 and its adjacent side rail 12, 13. A piston rod 23 projects from each cylinder 21 and is conventionally connected to the crosshead 15. Thus, as hydraulic fluid is introduced into the cylinders 21 at the right ends (unnumbered) thereof, the rods 23 will move to the left moving the crosshead 15 in the same direction, while hydraulic fluid introduced into the cylinders 21 at the left ends (unnumbered) thereof will retract the piston rods 23 into the cylinders 21 and move the crosshead 15 to the right. The crosshead 15 carries wheels 24 which move along tracks or rails 25 conventionally secured to the foundation 11. A pair of parallel guide plates 26 are fixed to the crosshead 15, project toward the carriage 14, and are each sandwiched between spaced pairs of guide rollers 27 which assure that the crosshead 15 will move along a straight path of travel, particularly under load upon the movement of the piston rods 23 to the left as viewed in FIG. 1.

The carriage or yoke assembly 14 can move along the side rails 12, 13, and is facilitated in such movement by a plurality of wheels 30 which are each schematically illustrated as individually being carried by a plate 31 secured to a top plate 35 of the carriage 14. The underside (unnumbered) of the carriage 14 is constructed to define two downwardly opening guide channels 33, 34 which are each of a lateral width to accommodate the respective side rails 12, 13. Aligned laterally oppositely projecting polygonal or square locking pins 36, 37 are slidably carried by the carriage 14 and each includes a handle 38 which projects through a slot (unnumbered) in the top plate 35. The handles 38 can be grasped to move the locking pins 36, 37 into polygonal/rectangular/square tubes 55 which are spaced along the length of each of the side rails 12, 13 and are welded thereto.

When it is desired to test a wire rope, a steel cable, a steel sling S or the like, opposite ends of the sling S or similar elongated member which is to be tested are conventionally secured to the carriage 14 and to the crosshead 15 by, for example, pins (not shown) of the carriage 14 and the crosshead 15 passing through loops L1, L2 of the sling S. Absent such loops L1, L2, the carriage 14 and/or the crosshead 15 can include a cable gripping block constructed in accordance with U.S. Pat. No. 4,874,152 in the name of Joseph E. Roberts et al. granted on Oct. 17, 1989.

The testing machine 10 has associated herewith suitable instrumentation, none of which is illustrated, but the same may include a conventional electronic strain gauge, digital readout meters, peak/hold digital readout meters, length displacement gauges and meters, an "X-Y" recorder for producing stress/strain curves, and similar instrumentation. The testing machine 10 can test wire cable, slings S or the like by subjecting the same to upwards of 3,000,000 lbs. over a length/pull of 206' from pin-to-pin between the carriage 14 and the crosshead 15. The maximum 3,000,000 lbs. loading is achieved by utilizing as each of the piston/cylinder mechanisms, 16, 17 a 1.5 million lbs. piston/cylinder mechanism having a stroke of approximately 132".

It will be appreciated that as the piston/cylinder mechanisms 16, 17 move the piston rods 23 to the left along with the crosshead 15, the sling S is progressively placed under tension and, of course, the side rails 12, 13 are placed under compression. Thus, these relatively long rails (200' long and beyond) must not only carry the compression loads for testing, but during a sling break test the rails instantaneously change from compression loading to tension loading when the sling S breaks due to the rebound or recoil effect. Heretofore conventional side rails were simply formed from heavy metal cross-sectioned rail members by making a 100% weld at the ends or butt joints of the rail members, and this created side rails that were both strong in tension and strong in compression. However, 100% welds at the joints requires a tremendous amount of heat and the rails warp and therefore are not straight which is essential to not only carry loads during testing but accurately reflect the test results. Such welds are also extremely costly and building machines by butt-welding rail members together to form long side rails is essentially cost prohibitive. Thus, while such conventional 100% buttwelded rail members might withstand the instantaneous changes from compression to tension loading when the sling breaks at, for example, 2,000,000 lbs., constructing such side rails in the conventional butt-welded manner practiced in the past was costly, ineffective, inefficient and prohibitive, particularly for high capacity testing machines on the order of upwards of the 3,000,000 lbs. machine having a 200' plus pin-to-pin pull length.

In accordance with the present invention, the side rails 12, 13 are identically constructed absent the 100% weld conventionally utilized in the past, and in lieu thereof each side rail 12, 13 is essentially fabricated as a composite reinforced structure which is herein described specifically relative to the rail 12 of FIGS. 2–6 of the drawings. This description of the manufacture of the side rail 12 is, of course, equally applicable to the side rail 13.

The side rail 12 is fabricated in a plurality of sections, there being three such side rail sections 41, 42 and 43 illustrated and numbered in FIGS. 1, 2 and 3 of the drawings. Obviously if the length of the side rail 12 is to be increased, additional rail sections corresponding to any one of the rail sections 41–43 would be utilized to extend the overall length of each of the side rails 12, 13.

The rail sections 41, 42 and 43 are identical to each other and each includes respective laterally spaced parallel steel rail members 44, 45; 46, 47; and 48, 49 with each rail member 44–49 having formed therein and therealong a plurality of polygonal/rectangular through openings 50 (FIG. 3) which are approximately 6"×6" in size. Each rail member 44–49 is a 2" thick steel plate approximately 19" in height and 45' long.

Before the rail sections 41–43 are aligned, as shown in FIGS. 2 and 3, each section 41–43 is individually fabricated by first welding a plurality of steel studs, preferably ¾"×6" studs, to the inner surfaces (unnumbered) of the rail members 44–49 which are each identified by the reference numeral 52. Nine such studs 52 are preferably welded to each end (unnumbered) of each of the rail members 44–49, and when the rail members 44–49 are eventually positioned in side-by-side parallel relationship to each other, as shown in FIG. 2, nine studs at each end of one of the rail members (46, for example) is aligned with nine studs at each end of the opposite rail member (47, for example) as is obviously apparent from FIGS. 2 and 3 of the drawings. Other such long studs 52 can be welded selectively along the center line of the rail members 44–49, as is illustrated by one such centrally located stud 52 welded to each of the rail members 44–49. The latter studs 52 are illustrated adjacent to shorter studs 53 (preferably ½"×4") which can be welded above the center line of the rail members 44–49 and selectively along the length of each rail member 44–49 which function in a manner to be described more fully hereinafter.

Eight studs 54, also ¾"×6" are welded in pairs to each of the corners (unnumbered) of each rectangular/polygonal/square (6"×6") steel tube 55 having ends which are located in the polygonal/square openings 50 and are welded to the respective associated rail members 44–49. At this point in the manufacture/fabrication of each of the rail sections or rail member sections 41–43, each rail section 41–43 is essentially an open top and bottom box-like frame defined by, for example, with respect to the rail section 42, the rail members 46, 47, the studs 52, 53 welded thereto and the tubes 55 having welded thereto the pairs of studs 54 and in turn being welded to the rail members 46, 47. The axial length of the tubes 55 is such as to hold the rail members 44, 45; 46, 47; 48, 49 in rigid, spaced, parallel relationship to each other at an inner distance of 15".

Steel reinforcement means 60 is next assembled within each of the rail sections 41–43. The steel reinforcement means 60 includes four #6 rebars 61–64 of approximately 45' in length associated with each rail section 41–43. As is best illustrated in FIG. 4, the rebars 61, 62 are supported upon the shorter studs 53 carried by the rail members 44, 45. A plurality of #3 steel stirrups 65 are suspended from the rebars 61, 62 and these in turn support the rebars 63, 64 along the length thereof. Appropriate wire (not shown) fastens the rebars 61–64 to the various stirrups 65 and to the short studs 53.

At this stage in the manufacture of the rails 12, 13, the thus fabricated rail sections 41–43 can be shipped from the manufacturing/fabricating site to the test site for final assembly and installation, or alternatively a very thin (⅛") steel plate 66 (FIG. 4) can be welded to the underside of, in bridging relationship to and along the entire length of the rail members 44, 45; 46–47; and 48, 49 and preferably project ¼" beyond the ends of each rail member 44–49. Alternatively, the plate 66 can be welded to the underside of the rail members 44, 45; 46, 47; and 48, 49 at the test site during final assembly.

At the test site (FIG. 1) the rail sections 41, 42 and 43 are aligned in parallelism with each other, noting in particular that the rail members 44, 46, 48 and 45, 47 and 49 are in coincident longitudinally aligned relationship. Moreover, there is a space or gap 71–74 of approximately ¼" between the opposing end faces (unnumbered) of the respective rail members 44, 46; 46, 48; 45, 47; and 47, 49. A 2"×1/16"×19" plate 75, 76 is welded to the respective outer and inner faces (unnumbered) of all of the rail members 44–49, as is best illustrated in FIG. 5 with respect to the rail members 44, 46. Since the bottom plates 66 earlier described each project ¼" beyond the end of each of the rail members 44–49, each ½" gap 71–74 is closed at its bottom by the abutment of adjacent plates 66, as is clearly illustrated in FIG. 5. Alternatively, if the plates 66 do not project beyond the ends of the rail members 44–49, an appropriate thin (⅛") steel plate can be welded to the under surfaces of any of the adjacent ends of the rail members 44–49 to close the bottoms of the respective spaces or gaps 71–74 for a purpose to be described more fully hereinafter. In either case each gap, space or dam 71–74 is open/accessible only from the top or above.

Additional steel reinforcement means 80 is located in spanning relationship between adjacent rail sections 41, 42 and 42, 43. The additional reinforcement means 80 is additional rebar varying in size (diameter) and length depending upon the rigidity desired to be imparted at the intersection or joint between each of the rail sections 41, 42 and 42, 43. In the present exemplary embodiment of the invention, the steel reinforcement means 80 includes sixteen rebars 81–96 (FIG. 4) approximately 4' long with the rebars 81–96 projecting an equal distance into each rail section 41, 42 and 42, 43, and being adjacent and wired to the respective rebars 61–64 (FIG. 4), the stirrups 65 and the studs 52 and 54. As thus far described the side rail 12 appears as illustrated in FIGS. 2 and 3.

The next step in the manufacture/final assembly of the side rail 12 and, of course, side rail 13, is to pour concrete C (FIGS. 1, 5 and 6) into the totality of the rail sections or frames 41, 42, 43 and any others aligned therewith, at which time the concrete C will, of course, surround, imbed and unitize the sections 41–43 upon subsequent solidification and/or cure. The concrete C fills the entire interior of the rail sections 41–43 of each of the rails 12 and 13 from the bottom plate 66 up to the upper edges (unnumbered) of the rail members 44–49, but does not enter the gaps or spaces 71–74 because of the plates 76, as is evident from FIG. 5.

After the concrete C has solidified/cured, a molten zinc alloy is poured into the gaps or spaces 71–74 filling each in its entirety and subsequently solidifying, as shown in FIG. 6, with the solidified zinc alloy being designated by the reference character Z. Thus, the compressive load during tensioning of the sling S (FIG. 1) will be carried by the solidified zinc alloy Z and, of course, by the concrete C and reinforcement means 60,80. The concrete C therefore not only stiffens each joint between the sections 41, 42 and 42, 43, but adds weight to the entire structure while all compressive loads are transferred between adjacent rail members 44, 46, for example, by the solidified zinc alloy Z therebetween. Preferably the additional reinforcement means 80 and each of the rebars 81–96 thereof are conventionally loaded to develop tension strength during solidification of the concrete C so that each joint between adjacent rail sections 41, 42 and 42, 43 of each rail 12 and 13 is strong in both compression and tension. Extremely strong loading is obviously available in compression because of the solidified zinc alloy Z in the gaps 71–74 between the opposing rail members 44, 46; 46, 48; 45, 47 and 47, 49, and because of the known high compressive strength of concrete, as well as the reinforcement means 60, 80 thereof. In addition, upon the sling S breaking under high tension load (2,000,000 lbs., for example), the rapid reversal of loading from compression to tension in the rail sections 41, 42 and 43 would be resisted by the rebar/reinforcement means 60, 80. Thus, the side rails 12, 13 can be manufactured perfectly straight in the absence of a 100% weld and thus will not warp or get out of alignment and the overall testing machine 10 can be manufactured efficiently time-wise and dollar-wise.

Although a preferred embodiment of the invention has been specifically illustrated and described herein, it is to be understood that minor variations may be made in the apparatus and the method without departing from the spirit and scope of the invention as defined in the appended claims.

I claim:

1. Equipment for testing a relatively elongated product comprising at least one rail, a carriage, first means for connecting a portion of a product which is to be tested to said carriage, second means for connecting a second portion of the product which is to be tested to said at least one rail, means for moving said carriage in a direction away from said second means to load the product in tension and incident thereto load the rail in compression, said rail having at least one joint, said joint including compression means for carrying a compression load when the product is loaded in tension, said joint further including tension means for absorbing tension loading upon the rail when the tension loading of the product is abruptly terminated, said rail including at least a pair of longitudinally aligned rail members having opposing ends in spaced relationship to define a space therebetween, and said joint compression means including material in situ molded in said space.

2. Equipment for testing a relatively elongated product comprising at least one rail, a carriage, first means for connecting a portion of a product which is to be tested to said carriage, second means for connecting a second portion of the product which is to be tested to said at least one rail, means for moving said carriage in a direction away from said second means to load the product in tension and incident thereto load the rail in compression, said rail having at least one joint, said joint including compression means for carrying a compression load when the product is loaded in tension, said joint further including tension means for absorbing tension loading upon the rail when the tension loading of the product is abruptly terminated, said rail including at least a pair of longitudinally aligned rail members having opposing ends in spaced relationship to define a space therebetween, and said joint tension means being in longitudinal spanning relationship to said space.

3. Equipment for testing a relatively elongated product comprising at least one rail, a carriage, first means for connecting a portion of a product which is to be tested to said carriage, second means for connecting a second portion of the product which is to be tested to said at least one rail, means for moving said carriage in a direction away from said second means to load the product in tension and incident thereto load the rail in compression, said rail having at least one joint, said joint including compression means for carrying a compression load when the product is loaded in tension, said joint further including tension means for absorbing tension loading upon the rail when the tension loading of the product is abruptly terminated, said rail including at least a pair of longitudinally aligned rail members having opposing ends in spaced relationship to define a space therebetween, and said joint compression means including metal in situ solidified in said space.

4. Equipment for testing a relatively elongated product comprising at least one rail, a carriage, first means for connecting a portion of a product which is to be tested to said carriage, second means for connecting a second portion of the product which is to be tested to said at least one rail, means for moving said carriage in a direction away from said second means to load the product in tension and incident thereto load the rail in compression, said rail having at least one joint, said joint including compression means for carrying a compression load when the product is loaded in tension, said joint further including tension means for absorbing tension loading upon the rail when the tension loading of the product is abruptly terminated, said rail including at least a pair of longitudinally aligned rail members having opposing ends in spaced relationship to define a space therebetween, said joint tension means being in longitudinal spanning relationship to said space, and said joint tension means including concrete.

5. Equipment for testing a relatively elongated product comprising at least one rail, a carriage, first means for connecting a portion of a product which is to be tested to said carriage, second means for connecting a second portion of the product which is to be tested to said at least one rail, means for moving said carriage in a direction away from said second means to load the product in tension and incident thereto load the rail in compression, said rail having at least one joint, said joint including compression means for carrying a compression load when the product is loaded in tension, said joint further including tension means for absorbing tension loading upon the rail when the tension loading of the product is abruptly terminated, said rail including at least a pair of longitudinally aligned rail members having opposing ends in spaced relationship to define a space therebetween, said joint tension means being in longitudinal spanning relationship to said space, and said joint tension means including longitudinally extending reinforcing bars.

6. Equipment for testing a relatively elongated product comprising at least one rail, a carriage, first means for connecting a portion of a product which is to be tested to said carriage, second means for connecting a second portion of the product which is to be tested to said at least one rail, means for moving said carriage in a direction away from said second means to load the product in tension and incident thereto load the rail in compression, said rail having at least one joint, said joint including compression means for carrying a compression load when the product is loaded in tension, said joint further including tension means for absorbing tension loading upon the rail when the tension loading of the product is abruptly terminated, said rail including at least a pair of longitudinally aligned rail members having opposing ends in spaced relationship to define a space therebetween, said joint tension means being in longitudinal spanning relationship to said space, and said joint tension means including longitudinally extending rebar.

7. Equipment for testing a relatively elongated product comprising at least one rail, a carriage, first means for connecting a portion of a product which is to be tested to said carriage, second means for connecting a second portion of the product which is to be tested to said at least one rail, means for moving said carriage in a direction away from said second means to load the product in tension and incident thereto load the rail in compression, said rail having at least one joint, said joint including compression means for carrying a compression load when the product is loaded in tension, said joint further including tension means for absorbing tension loading upon the rail when the tension loading of the product is abruptly terminated, said rail including at least a pair of longitudinally aligned rail members having opposing ends in spaced relationship to define a space therebetween, said joint tension means being in longitudinal spanning relationship to said space, and said joint tension means including concrete and longitudinally extending reinforcing bars embedded therein.

8. Equipment for testing a relatively elongated product comprising at least one rail, a carriage, first means for connecting a portion of a product which is to be tested to said carriage, second means for connecting a second portion of the product which is to be tested to said at least one rail, means for moving said carriage in a direction away from said second means to load the product in tension and incident thereto load the rail in compression, said rail having at least one joint, said joint including compression means for carrying a compression load when the product is loaded in tension, said joint further including tension means for absorbing tension loading upon the rail when the tension loading of the product is abruptly terminated, said rail including at least a pair of longitudinally aligned rail members having opposing ends in spaced relationship to define a space therebetween, said joint tension means being in longitudinal spanning relationship to said space, and said joint tension means including concrete and longitudinally extending rebar embedded therein.

9. Equipment for testing a relatively elongated product comprising at least one rail, a carriage, first means for connecting a portion of a product which is to be tested to said carriage, second means for connecting a second portion of the product which is to be tested to said at least one rail, means for moving said carriage in a direction away from said second means to load the product in tension and incident thereto load the rail in compression, said rail having at least one joint, said joint including compression means for carrying a compression load when the product is loaded in tension, said joint further including tension means for absorbing tension loading upon the rail when the tension loading of the product is abruptly terminated, said rail including two pair of first and second longitudinally aligned rail member having opposing ends in spaced relationship to define a space between each of said pair of rail members, said joint compression means including material in situ solidified in each of said spaces, and said joint compression means being in longitudinal spanning relationship across said spaces.

10. The testing equipment as defined in claim 9 wherein said joint compression means includes concrete.

11. The testing equipment as defined in claim 10 wherein said material is metal.

12. The testing equipment as defined in claim 9 wherein said joint compression means includes longitudinally extending reinforcing bars.

13. The testing equipment as defined in claim 12 wherein said material is metal.

14. The testing equipment as defined in claim 9 wherein said joint compression means includes longitudinally extending rebar.

15. The testing equipment as defined in claim 14 wherein said material is metal.

16. The testing equipment as defined in claim 9 wherein said joint compression means includes concrete and longitudinally extending reinforcing bars embedded therein.

17. The testing equipment as defined in claim 16 wherein said material is metal.

18. The testing equipment as defined in claim 9 wherein said joint compression means includes concrete and longitudinally extending rebars embedded therein.

19. The testing equipment as defined in claim 18 wherein said material is metal.

20. The testing equipment as defined in claim 9 wherein said material is metal.

21. The testing equipment as defined in claim 9 wherein said material is metal alloy.

22. The testing equipment as defined in claim 9 wherein said material is zinc alloy.

* * * * *